(12) United States Patent
Wong

(10) Patent No.: US 6,713,287 B1
(45) Date of Patent: Mar. 30, 2004

(54) ENZYMATIC SYNTHESIS OF L-FUCOSE AND L-FUCOSE ANALOGS

(75) Inventor: Chi-Huey Wong, Rancho Sante Fe, CA (US)

(73) Assignee: The Scripps Research Institute, La Jolla, CA (US)

( * ) Notice: Subject to any disclaimer, the term of this patent is extended or adjusted under 35 U.S.C. 154(b) by 0 days.

(21) Appl. No.: 08/547,602

(22) Filed: Oct. 24, 1995

(51) Int. Cl.$^7$ ................................................ C12P 19/02
(52) U.S. Cl. .......................... 435/105; 435/94; 435/72
(58) Field of Search ............................ 435/105, 94, 72

(56) References Cited

U.S. PATENT DOCUMENTS 3,240,775 A    3/1966    Schweiger ................... 536/124

OTHER PUBLICATIONS

Chiba, et al., "A New Synthesis of alpha–L–Fucose", *Chem. Pharm. Bull*, 27: 2838–2840 (1979).
Chou, et al., " A New Route to Deoxythiosugars Based on Aldolases", *J. Am. Chem. Soc.*, 116:6191–6194 (1994).
Defaye, et al., "Synthese Des D–Fucose Et L–(3–2H) Fucose A Partir DuD–Mannose" *Carbohydrate Research*, 95:131–141 (1981).
Dejter–Juszynski, et al., "Synthesis of L–Fucose", *Carbohydrate Research*, 28: 144–146 (1973).
Durrwachter, et al., "Enzymatic Aldol Condensation/Isomerization as a Route to Unusual Sugar Derivatives", *J. Am. Chem. Soc.*, 108: 7812–7818 (1986).
Fessner, et al., "Diastereoselective Enzymatic Aldol Additions: L–Rhamnulose and L–Fuculose 1–Phosphate Aldolases from *E–coli*", *Angew. Chem. Int*. 30:555–558 (1991).
Fessner, et al., "6–Deoxy–L–lyxo– and 6–Deoxy–L–arabino–hexulose 1–phosphates. Enzymic Syntheses by Antagonistic Metabolic Pathways", *Tetrahedron: Assymetry* 4:1183–1192 (1993).

Fessner, et al., "Enzymatic Syntheses of Rare Ketose 1–Phosphates", *Tetrahedron Letters*, 33: 5231–5234, (1992).
Gesson, et al., " A Short Synthesis of L–Fucose and Analogs from D–Mannose", *Tetrahedron Letters*, 33: 3637–3640 (1992).
Green, et al.,"Enzymatic Conversion of L–Fucose to L–Fuculose", *J. Biol. Chem*. 219:557–568 (1956).
Garcia–Junceda, et al., " A New Strategy for the Cloning, Overexpression,and One Step Purification of Three DHAP–Dependent Aldolases: . . . ", *Bioorganic & Medicinal Chemistry*, 3: 945–953 (1995).
Liu, et al., "Use of Dihydroxyacetone Phosphate Dependent Aldolases in the Synthesis of Deoxyazasugars", *J. Org. Chem.*, 56: 6280–6289 (1991).
Tanimura, Akio, *Chem. Abstracts*, 55:12306 (1961).
Williams, et al., "Further Experiments on the Oxidation of Sugar Acetals and Thioacetals by Acetobacter Suboxydans", *Can. J. Chem.*, 45:741–744 (1967).

*Primary Examiner*—Francisco Prats
(74) *Attorney, Agent, or Firm*—Morgan, Lewis & Bockius, LLP

(57) ABSTRACT

Fucose and fucose analogs are synthesized enzymatically in a three step synthetic protocol. In the first step, L-fuculose-1-phosphate of analog thereof is produced by means of an aldolase catalyzed aldol addition reaction. In the second step, the fuculose-1-phosphate or analog thereof is dephosphorylated to form L-fuculose or an analog thereof using acid dephosphorylase as a catalyst. In the third step, the L-fuculose or analog thereof is converted to L-fucose or an analog thereof using L-fucose isomerase as a catalyst. The synthesis may be a one pot reaction involving the addition substrates and each of the above enzymes to a single reaction vessel. Alternatively, the synthesis may be carried out with purification steps after each reaction.

1 Claim, 4 Drawing Sheets

ENZYMATIC SYNTHESIS OF L-FUCOSE AND L-FUCOSE ANALOGS

STATEMENT OF GOVERNMENT RIGHTS

This invention was made with government support under a National Institutes of Health Grant No. GM 44154. The government has certain rights in the invention.

FIELD OF THE INVENTION

The invention relates to methods for synthesizing L-fucose and L-fucose analogs. More particularly, the invention is directed to enzymatic methods for synthesizing L-fucose and L-fucose analogs and to the L-fucose analogs synthesized thereby.

BACKGROUND

L-fucose 1 is a naturally occurring sugar widely found in Nature. It is found in many bacterial and plant glycosides and polysaccharides (Lindberg et. al., *MTP Int. Rev. Ser. One, Carbohydr.* 1973, 7, 319; Jann, X et. al. In I. W. Shutherland (Ed.), *Surface Carbohydrates of the Prokaryotic Cell*, Academic Press, New York, 1977, pp 247–287; Aspinall, G. O. et. al. *MTP Int. Rev. Sci., Ser. One, Carbohydr.* 1973, 7, 285). L-fucose is 25 sometimes found sulfated (Percival, E et. al. *Methods Carbohydr. Chem.* 1962, 1, 195; Larsen, B et. al., *Acta Chem. Scand.* 1966, 20, 219; Chandrasekaran, E. V. et. al. *Biochemistry* 1995, 34, 2925). It has also been found in oligosaccharides of human milk (Kobata, A. In M. I. Horowitz, W. Pigman (Eds.), *The Glycoconjugates*, Vol. 1, Academic Press, New York, 1977, pp 423–440). In addition, L-fucose is found in many glycolipids (Hakomori, S.-I. *Prog. Biochem. Pharmacol.* 1975, 10, 167; Mckibbin, J. M. *J. Lipid Res.* 1978, 19, 131) and glycoproteins including several families of blood-group antigens (Loyd, K. O. *MTP Int. Rev. Sci., Ser. Two, Carbohydr.* 1976, 7, 251; Kornfeld et. al. *Annu. Rev. Biochem.* 1976, 45, 217). It is found in cell-surface oligosaccharides, such as the tetrasaccharide sialyl Lewis x ($Le^x$) on neutrophils, as part of selectin ligands involved in cell adhesion (Phillips, M. et. al. *Science* 1990, 250, 1130; Waltz, G. et. al., *Science* 1990, 250, 1132; Lowe, J et. al. *Cell* 1990, 63, 475) and cancer metastasis processes (Paulson, J. C. In *The Receptors*; Conn, M., Ed.; Academic Press: New York, 1985; Vol. 2, pp 131–219; Paulson, J. C. *In Adhesion: its role in inflammatory disease*; Harlan, J.; Liu, D., Eds.; W. H. Freeman: New York, 1992; Chapter 2, p 19; Springer, T. et. al. *Nature* 1991, 349, 196; Lasky, L. *Science* 1992, 258, 964; Rice, G. et. al. *Science* 1989, 246, 1303; Bevilacqua, M P et. al. *Proc. Natl. Acad. Sci. U.S.A.* 1987, 84, 9238.

Given the importance of sialyl $Le^x$ and derivatives as potential therapeutic agents for the treatment of inflammatory diseases, the development of an efficient synthesis of 1 has been a subject of interest in glycotechnology (Wong et. al. *J. Am. Chem. Soc.* 1992, 114, 9283; Wong, et. al. *J. Am. Chem. Soc.* 1993, 115, 7549; Wong, et. al. *J. Am. Chem. Soc.* 1995, 117, 66; Mulligan, M. S. et. al. *Nature* 1993, 364, 149; Flowers, H. M. *Adv. Carbohydr. Chem. Biochem.* 1981, 39, 279).

Organic synthesis may be employed to produce L-fucose 1. Tanimura discloses an organic synthesis of L-fucose 1 in 9 steps with a 1% overall yield, starting from L-arabinose (Tanimura, A. et. al. *Eisei Shikenjo Hokoku* 1959, 77, 123; *Chem. Abstr.* 1961, 55, 12306). An improved organic synthesis of L-fucose 1 is disclosed by Dejter-Juszyzynski using D-galactose as a starting material and providing a 15% overall yield (4.88 mmol) in 4 steps (Dejter-Juszynski, M. et. al. *Carbohydr. Res.* 1973, 28, 144). A synthesis for the preparation of L-fucose from D-glucose has produced 19.3% of L-fucose and afforded 1.69 mmol of L-fucose in 5 steps (Chiba, T., *Chem. Pharm. Bull.* 1979, 27, 2838). L-fucose has also been synthesized using D-mannose in 54.8% yield and 6 steps (Gesson, J. et. al. *Tetrahedron Lett.* 1992, 33, 3637) or using methyl α-D-mannopyranoside in 24% overall yield affording 0.26 mmol of L-fucose in 8 steps (Wong, C.-C. *Carbohydr. Res.* 1981, 95, 131). In general, the known organic syntheses of L-fucose 1 employ multichemical transformations and result in low yields.

There is no known method for synthesizing L-fucose 1 enzymatically.

Commercially, L-fucose 1 is obtained from natural sources. The preferred natural source is Fucoidan, i.e. a substance extracted from kelp (Schweiger, R. G. (To Kelco Co.), U. S. Pat. No. 3,240,775 Mar. 15, 1966, Appl. Jul. 30, 1962; *Chem. Abstr.* 1966, 65, 2342).

The synthesis of L-fuculose-1-phosphate 4 has been previously carried out from dihydroxyacetone phosphate 2 and L-lactaldehyde 3 via recombinant L-fuculose aldolase-catalyzed aldolic condensation. In addition, the synthesis of L-fuculose-1-phosphate 4 has been performed via L-fucose isomerase-catalyzed isomerization of L-fucose 1, coupled with L-rhamnulose kinase (Fessner et. al. *Tetrahedron: Asymmetry* 1993, 4, 1183; Fessner et. al. *Angew. Chem. Int. Ed. Engl.* 1991, 30, 555; Fessner et. al. *Tetrahedron Lett.* 1992, 33, 5231; Wong, C.-H. et. al. *J. Org. Chem.* 1991, 56, 6280). D/L lactaldehyde dimethylacetal 6 has been synthesized and reported by Wong et. al. *J. Am. Chem. Soc.* 1986, 108, 7812.

L-fuculose 5 has been prepared from L-fucose 1 using a cell free extract of an *E. coli* mutant strain in the presence of a borate buffer (Green, M.; Cohen, S. S. *J. Biol. Chem.* 1956, 219, 557) via bacterial oxidation of L-fucitol by Aerobacter suboxidans (Williams, D. T.; Jones, J. K. N. *Can. J. Chem.* 1967, 45, 741) and from 4 via enzyme-catalyzed phosphate hydrolysis (Fessner et. al. *Tetrahedron: Asymmetry* 1993, 4, 1183; Wong, C.-H. et. al. *J. Org. Chem.* 1991, 56, 6280).

L-fuculose-1-phosphate aldolase is prepared from recombinant *E.Coli* cells using the methodology as described in Wong, C.-H. et. al. *J. Am. Chem. Soc.* 1994, 116, 6191 and Wong, C.-H. *Bioorg. Med. Chem.* 1995, 3, 945. *E.coli* which express recombinant aldolase may be obtained from American Type Culture Collection (ATCC number 86984). *E.coli* which express recombinant isomerase may be obtained from American Type Culture Collection (ATCC number 87024). Acid phosphatase is commercially available and can be purchased from Sigma chemical company.

What is needed is a simple method for enzymatically synthesizing L-fucose 1 and L-fucose analogs for providing good yields at low cost.

SUMMARY

One aspect of the invention is directed to a method for enzymatically synthesizing L-fucose and L-fucose analogs. The method for enzymatically synthesizing L-fucose includes three steps, viz. providing L-fuculose-1-phosphate, enzymatically converting the L-fuculose-1-phosphate to L-fuculose; and then enzymatically converting the L-fuculose to L-fucose.

In a preferred mode, the L-fuculose-1-phosphate is obtained by means of an aldol addition reaction between dihydroxyacetone phosphate and DL-lactaldehyde catalyzed by aldolase or more particularly by L-fucolose-1-phosphate aldolase. The DL-lactaldehyde may be obtained by conversion from DL-lactaldehyde dimethylacetal. In one mode of the invention, the L-fuculose-1-phosphate is purified after its production by the aldol addition reaction and prior to its conversion to L-fuculose. In an alternative mode of the invention, the L-fuculose-1-phosphate is not purified after the aldol addition reaction, i.e., it is employed without purification in a dephosphorylation reaction which converts the L-fuculose-1-phosphate to L-fuculose. In this later instance, the aldol condensation reaction and the dephosphorylation reaction may be performed in a single reaction vessel.

In a preferred mode the dephosphorylation of L-fuculose-1-phosphate to form L-fuculose is catalyzed by acid phosphatase (E.C. 3.1.3.2). The isomerization of the L-fuculose to form L-fucose may then be catalyzed by L-fucose isomerase. In one mode of the invention, the L-fuculose is purified prior to its isomerization to L-fucose. In an alternative mode of the invention, the L-fuculose is not purified, i.e., it is employed without purification in the isomerization reaction which converts the L-fuculose to L-fucose. In this later instance, the dephosphorylation reaction and the isomerization reactions may be performed in a single reaction vessel.

A second aspect of the invention is directed to a method for enzymatically synthesizing L-fucose analogs represented by the following structure:

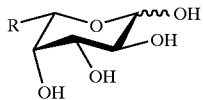

wherein R is a substituent selected from the group consisting of H, —CH$_2$, Et, —CH$_2$N$_3$, and —CH$_2$OMe. The method for enzymatically synthesizing L-fucose analogs includes three steps, viz. an enzymatically catalyzed aldol addition reaction for converting a substrate to a first intermediate, an enzymatically catalyzed dephosphorylation for converting a first intermediate to a second intermediate, and an enzymatically catalyzed isomerization for converting the second intermediate to the L-fucose analog.

In a preferred mode of this second aspect of the invention, an aldolase is employed for catalyzing the aldol addition reaction for converting a substrate to a first intermediate. A preferred substrate is a compound represented by the following structure:

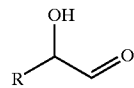

wherein R is a substituent selected from the group consisting of H, —CH$_2$, Et, —CH$_2$N$_3$, and —CH$_2$OMe. A preferred aldolase is L-fuculose-1-phosphate aldolase. The product of the aldol addition reaction is the first intermediate, represented by the following structure:

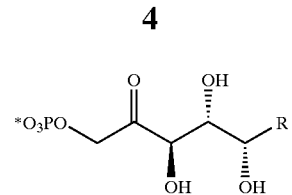

wherein R is a substituent selected from the group consisting of H, —CH$_2$, Et, —CH$_2$N$_3$, and —CH$_2$OMe. The first intermediate is then converted to a second intermediate in a reaction catalyzed by acid phosphatase (E.C. 3.1.3.2). The second intermediate is represented by the following structure:

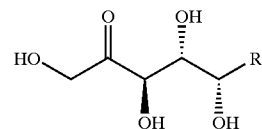

wherein R is a substituent selected from the group consisting of H, —CH$_2$, Et, —CH$_2$N$_3$, and —CH$_2$OMe. The second intermediate is then converted to the L-fucose analog in a reaction catalyzed by L-fucose isomerase.

In one mode of the invention, the first intermediate is purified after its production by an aldol addition reaction and prior to its conversion to the second intermediate. In an alternative mode of the invention, the first intermediate is not purified after the aldol addition reaction, i.e., it is employed without purification in a dephosphorylation reaction which converts the first intermediate to the second intermediate. In this instance, the condensation reaction and the dephosphorylation reaction may be performed in a single reaction vessel.

In a preferred mode the dephosphorylation of the first intermediate to form the second intermediate is catalyzed by catalyzed by acid phosphatase (E.C. 3.1.3.2). The isomerization of the second intermediate to form the L-fucose analog may then be catalyzed by L-fucose isomerase. In one mode of the invention, the second intermediate is purified prior to its isomerization to form the L-fucose analog. In an alternative mode of the invention, the second intermediate is not purified, i.e., it is employed without purification in the isomerization reaction to form the L-fucose analog. In this later instance, the dephosphorylation reaction and the isomerization reactions may be performed in a single reaction vessel.

A third aspect of the invention is directed to a method for enzymatically synthesizing L-fucose analogs represented by the following structure:

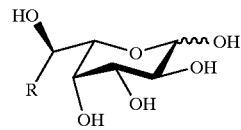

wherein R is Me. The method for enzymatically synthesizing L-fucose analogs includes three steps, viz. an enzymatically catalyzed aldol addition reaction for converting a substrate to a first intermediate, an enzymatically catalyzed dephosphorylation for converting a first intermediate to a second intermediate, and an enzymatically catalyzed isomerization for converting the second intermediate to the L-fucose analog.

In a preferred mode of this third aspect of the invention, an aldolase is employed for catalyzing the aldol addition reaction for converting a substrate to a first intermediate. A preferred substrate is a compound represented by the following structure:

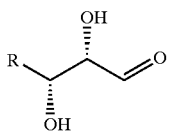

wherein R is Me. A preferred aldolase is L-fuculose-1-phosphate aldolase. The product of the aldol addition reaction is the first intermediate, represented by the following structure:

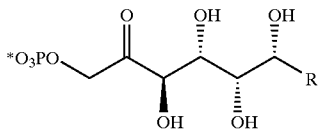

wherein R is Me.

The first intermediate is then converted to a second intermediate in a reaction catalyzed by acid phosphatase (E.C. 3.1.3.2). The second intermediate is represented by the following structure:

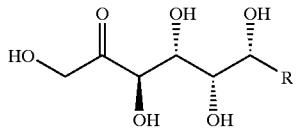

wherein R is Me. The second intermediate is then converted to the L-fucose analog in a reaction catalyzed by L-fucose isomerase.

In one mode of the invention, the first intermediate is purified after its production by means of an aldol addition reaction and prior to its conversion to the second intermediate. In an alternative mode of the invention, the first intermediate is not purified after the aldol addition reaction, i.e., it is employed without purification in a dephosphorylation reaction which converts the first intermediate to the second intermediate. In this instance, the aldol addition reaction and the dephosphorylation reaction may be performed in a single reaction vessel.

In a preferred mode the dephosphorylation of the first intermediate to form the second intermediate is catalyzed by catalyzed by acid phosphatase (E.C. 3.1.3.2). The isomerization of the second intermediate to form the L-fucose analog may then be catalyzed by L-fucose isomerase. In one mode of the invention, the second intermediate is purified prior to its isomerization to form the L-fucose analog. In an alternative mode of the invention, the second intermediate is not purified, i.e., it is employed without purification in the isomerization reaction to form the L-fucose analog. In this later instance, the dephosphorylation reaction and the isomerization reactions may be performed in a single reaction vessel.

A fourth aspect of the invention is directed to the compound synthesized by the method of the third aspect of the invention and represented by the following structure:

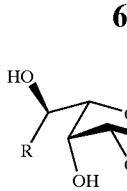

wherein R is Me.

DETAILED DESCRIPTION

Figure 1:
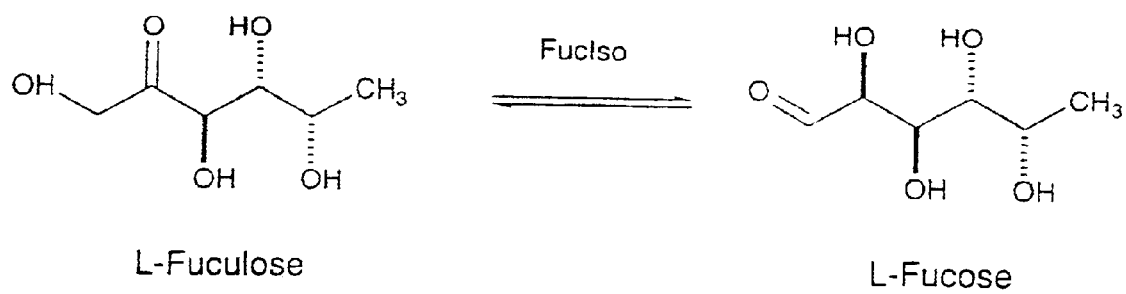
FIG. 1 illustrates the reaction catalyzed in vivo by fucose isomerase (FucIso)
Figure 2:
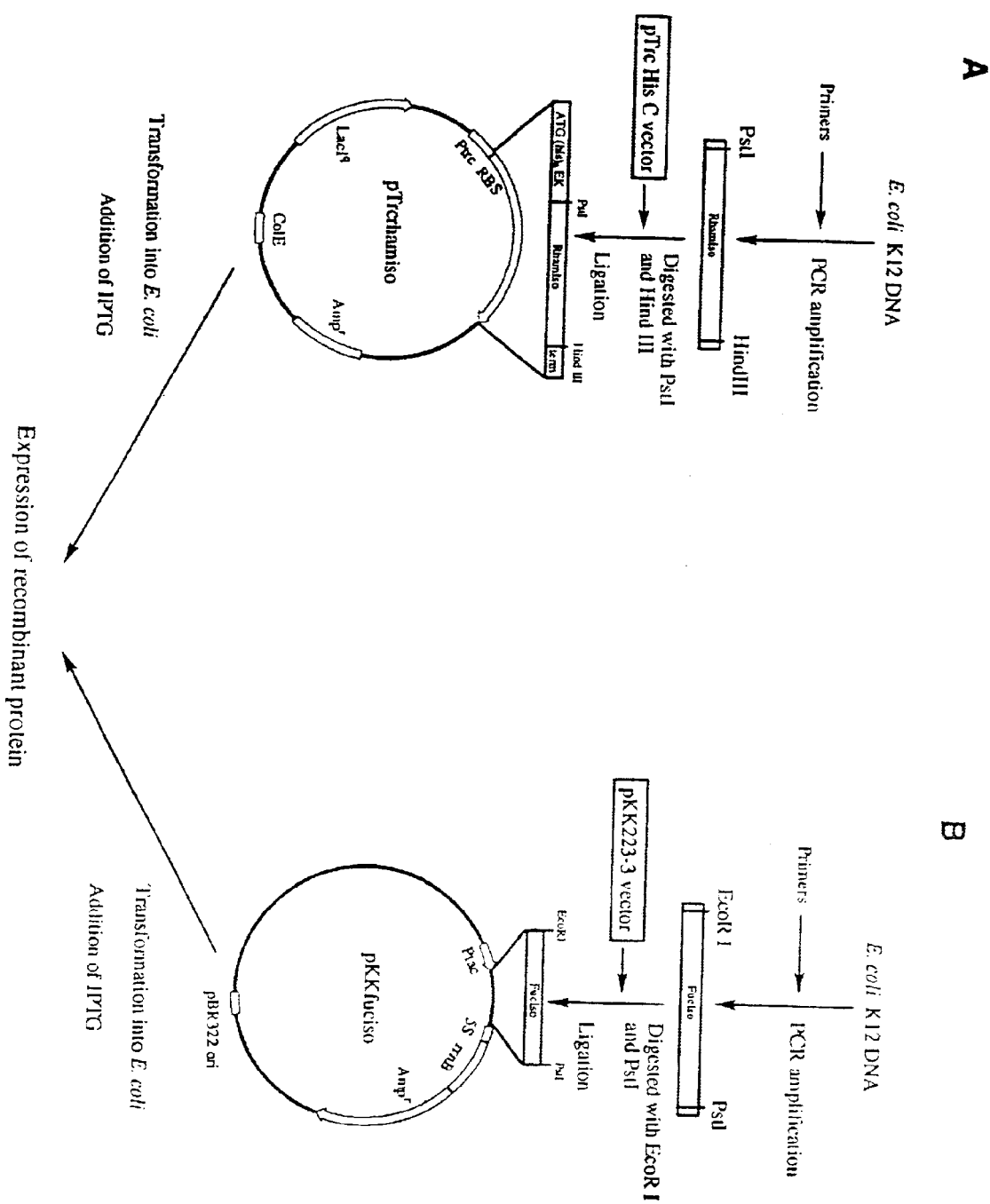
FIG. 2 illustrates the strategy for the cloning of A) Rhamnose isomerase and B) fucose isomerase (FucIso). The main characteristics of the expression vectors are shown.

Materials and Methods. Acid phosphatase (E.C. 3.1.3.2) was purchased from Sigma. All chemicals and solvents were purchased from Aldrich. Dowex 50W-X8 (200–400 mesh, $H^+$ form) was thoroughly washed with purified water prior to use. Aldol addition reaction was monitored enzymatically by dihydroxyacetone phosphate (DHAP) consumption (Bergmeyer, H. U. *Methods of Enzymatic Analysis*, 3rd Ed., Vol 2, Verlag Chemie: Deerfield, Fla., 1984, pp 146–7). The phosphatase-catalyzed hydrolysis was monitored by TLC (silica gel 60 from Merck). Isomerization was monitored by $^{13}$C-NMR (100 MHZ) analysis of the methyl group of L-fucose 1 ($\delta$=15.9 ppm) and L-fuculose 5 ($\delta_{mayor}$=15.0 ppm, $\delta_{Meminor}$=14.0 ppm) in the cyclized form. Nuclear magnetic resonance ($^1$H: 400 MHZ; $^{13}$C: 100 MHZ) spectra were obtained using HDO (in $D_2O$; $\delta$=4.8 ppm) and $CH_3CN$ (in $D_2O$; $\delta$=1.30 ppm) as internal references. Flash chromatography was carried out with silica gel 60 (230–400 mesh).

Enzyme preparation. The *E. coli* cells containing recombinant L-fucose isomerase prepared in this laboratory (described infra) and deposited with American Type Culture Collection (ATCC), (ATCC#87024) were grown aerobically to late logarithmic phase ($OD_{600}$ 0.9) at 37° C. in four 3 liter flasks containing LB medium (1L each; commercially available from Sigma) supplemented with ampicillin (250 mg/mL; commercially available from Sigma), followed by induction with isopropyl-β-D-thio-galactopyranoside The culture was kept overnight ($OD_{600}$ 2.1) at 30° C. Cells were harvested by centrifugation (10,000×g; 30 g of wet cells were obtained), resuspended in Tris-HCl buffer (50 mM, pH 7.5, 80 mL) and disrupted by repeatedly passing through a French Press ($^-$1600 lb/in$^2$) five times. Cellular debris was removed by centrifugation (16,000×g) and the clear supernatant (total activity 66000 units) was used for isomerization reaction. For the preparation of aldolase, the *E. coli* cells prepared in this laboratory and deposited with ATCC (ATCC#86984) were grown as previously described and the crude extract (total activity 1720 units) obtained was directly used for aldol reaction (aldolase preparation from the procedure as described in Wong, C.-H. et. al. *J. Am. Chem. Soc.* 1994, 116, 6191; Wong, C.-H. et. al. *Bioorg. Med. Chem.* 1995, 3, 945). The aldolase and isomerase were assayed according to the procedures described in Dische, Z.; Borenfreund, E.; *J. Biol. Chem.* 1951, 192, 583. One unit of enzyme represents one micromole of product formed per minute. *Preparation of Fucose isomerase* (FucIso)

Fucose isomerase was overexpressed in *E. coli*, purified and characterized. The fucose isomerase gene was ligated to the EcoRI and PstI sites of vector pKK223-3 for overexpression of the enzymes in *E. coli* XL1-Blue MRF'. Approximately 16,500 U of active fucose isomerase can be obtained per liter of culture from these expression systems. In this case, the preparation of the crude extract by freezing and thawing allows us to purify the enzyme also by a single chromatography step.

Figure 3:
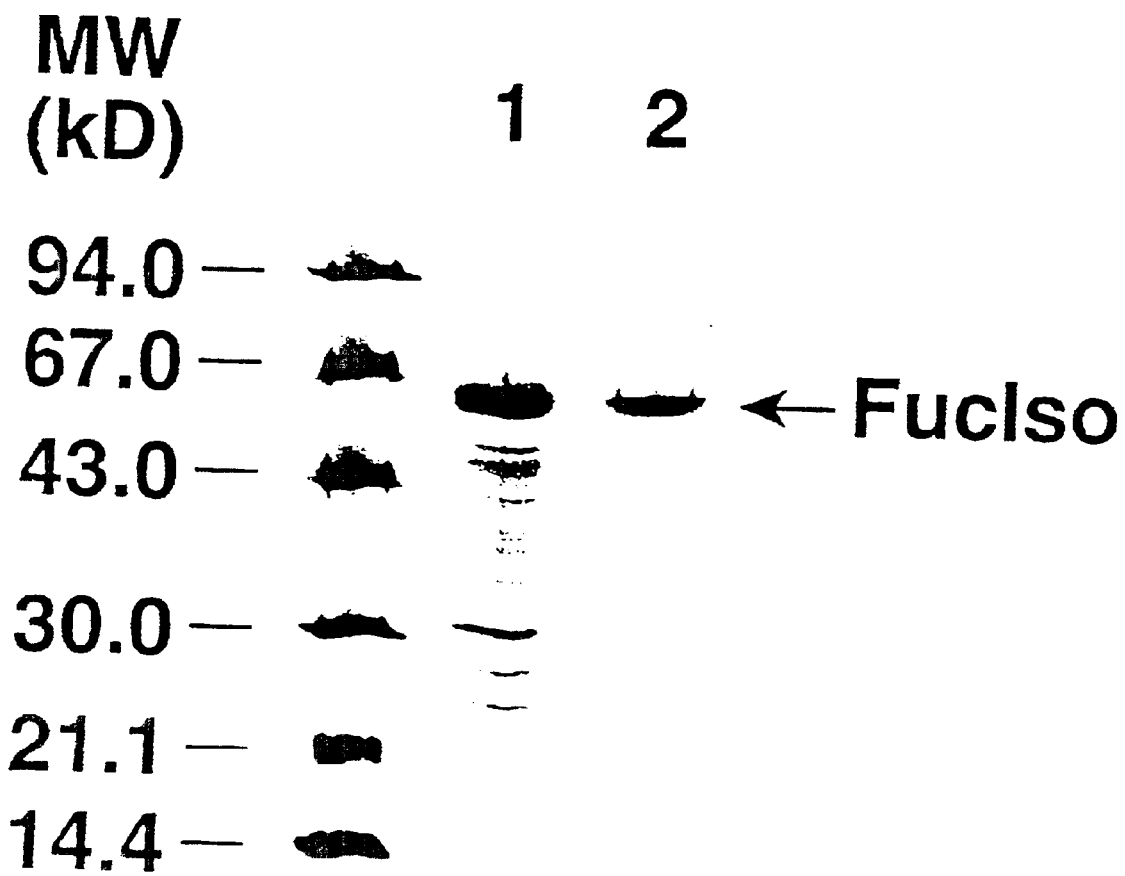
FIG. 3 illustrates the monitoring of fucose isomerase (FucIso) expression during the culture time. The first lane shows the crude extract after four cycles of freezing and thawing. In this case, the crude protein was used as a standard. Lane 0 illustrates an aliquot taken before induction and analyzed by SDS-PAGE. Lane 1 indicates an aliquot taken one hour after induction and analyzed by SDS-PAGE. Lane 3 represents an aliquot taken at 3 hours after induction. The maximum accumulation is observed 3 hours after induction. Lane 18 illustrates that the enzyme remained stable after 18 hours of cultivation. The production of FucIso in these conditions is about 16,500 U/L (approximately 2,640 U/g of cell).

IPTG (isopropyl β-D thiogalactopyranose), the enzymes were expressed as inclusion bodies. The formation of inclusion bodies can be avoided by dropping the cultivation temperature. In the expression of FucIso, when the temperature was dropped to 30° C. the enzyme was obtained in a soluble form and was the major band detected in the gel (FIG. 3). The expression of FucIso reached a maximum 3 h after the induction, and the enzyme remained stable in a long period of cultivation (FIG. 3). However, accumulation of the enzyme in overnight culture did not differ significantly from that found in the first three hours of cultivation (FIG. 3). The production of FucIso in these conditions is about 16,500 U/L (≈2,640 U/g of cell). Because of these results, we attempted solubilization of the inclusion bodies. The pellet, obtained after disruption of the cells harvested from 1-L culture at 30° C., was resuspended in 10 mL of distilled water. Urea was then added to the suspension to a final concentration of 6 M. After 1 h of incubation at room temperature, the suspension was centrifuged at 12,000×g for 30 min. The solubilization of the inclusion bodies was checked by SDS-PAGE of the supernatant. The urea was removed slowly by dialysis against a total of 12 L of Tris-HCl buffer (50 mM, pH 7.6) with three changes during 36 h. After dialysis the sample was again centrifuged as above, and the supernatant analyzed by SDS-PAGE to check the presence of the soluble protein. The activity of the soluble enzyme from the inclusion bodies was determined by the cysteine-carbazol method (Dische, Z.; Borenfreund, E. *J. Biol. Chem.* 1951, 192, 583) and was found to be about 2,400 U/L of culture and the

TABLE I

Primers and restriction sites used for the cloning of RhamIso and FucIso

| Isomerase | Restriction enzyme at 5' | Restriction enzyme at 3' | N-Terminal Primer (5' → 3') | C-Terminal Primer (5' → 3') |
| --- | --- | --- | --- | --- |
| RhamIso | PstI | HindIII | ATATTCTGCAGACCACTCAACTGGAA | GGCGCAAGCTTTTACCTGCTGGCGTATCGTGT |
| FucIso | EcoRI | PstI | ATATTGAATTCAACATGAAAAAAATCAGCTTACCG | GCGCCTGCAGTTAAACGCTTGTACAACGGA |

Cloning of FucIso.

For each target gene two primers were designed to specifically complement the C-terminal and N-terminal gene sequences of fucI (Lu, Z. and Lin, E. C. C. *Nucleic Acid Res.* 1989, 17, 4883). Each primer included the recognition sequence for the restriction enzymes chosen to clone the insert. The sequences of the primers and the cleavage sites for restriction enzymes used for each gene are shown in Table I. The PCR amplifications were quite specific, and only one band with a molecular weight consistent with that previously reported (1.8 kb respectively for fucI) was observed. After the ligation of digested vector and inserts, the DNA's were transformed into *E. coli* XL1-Blue MRF' strain and plated on LB-ampicillin plates. Out of 20–25 colonies selected for each gene, seven to ten colonies carried the desired insert. The Tac promoter in the pKK223-3 vector, can be induced by IPTG (isopropyl β-D thiogalactopyranose).

Expression of Recombinant FucIso.

Figure 4:
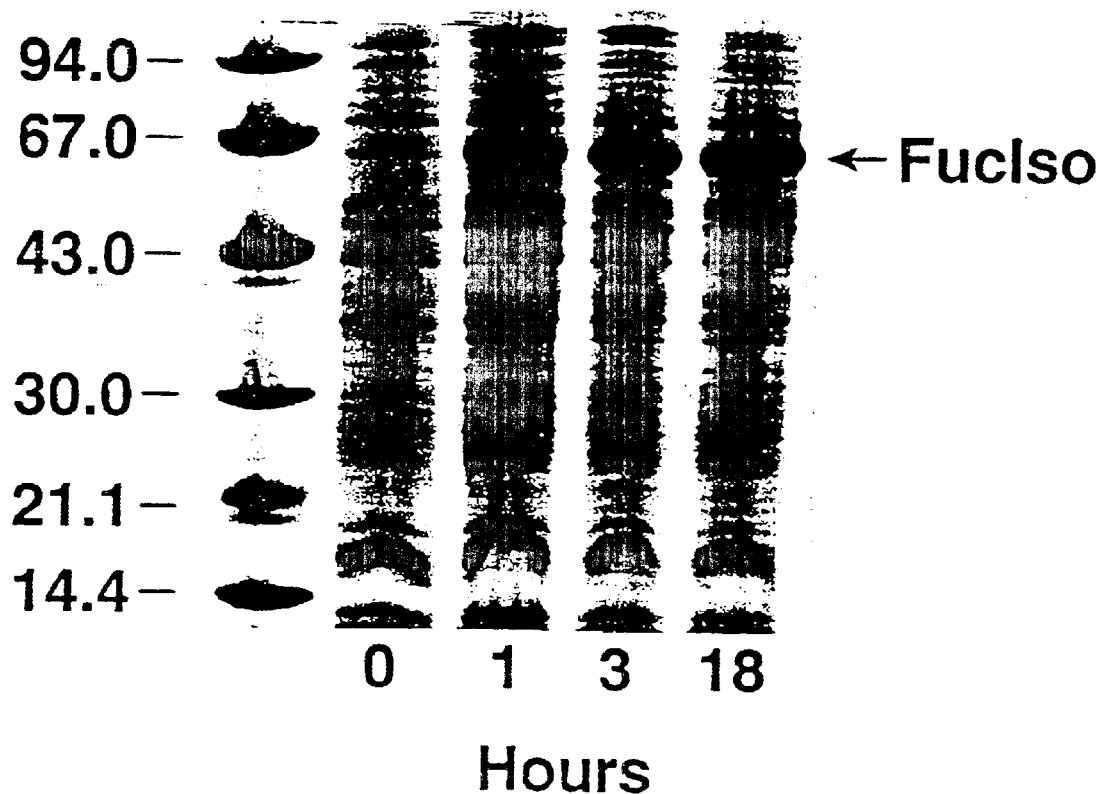
FIG. 4 illustrates the SDS-PAGE of the fucose isomerase (FucIso) purification. Lane 1 shows the crude extract after four cycles of freezing and thawing. In this case, the protein was not obtained in a completely pure form. Lane 2 illustrates further purification of the fucose isomerase by using high performance liquid chromatography using a Mono Q column (anion exchange) with a gradient between 0.2 and 0.5 M of NaCl. This provided the enzyme in a completely pure form as shown as a single band.

The clones were grown on LB medium containing 250 μg/mL ampicillin and induced with IPTG (isopropyl β-D thiogalacto pyranose) as described infra. The expression level of the enzyme was followed with time and examined with SDS-PAGE. The expression of the these enzymes was strongly dependent of the cultivation temperature. When the cells were grown at 37° C. after induction with 150 μM of specific activity shown by RhamIso in this condition was 108.6 U/mg of protein. This method of preparing active enzyme is simple and can be applied to a larger volume of sample, with the advantage of obtaining the enzyme in a relatively pure form (FIG. 4) to be used directly in organic synthesis.

One Step Purification of FucIso.

Recently it has been reported that recombinant proteins can be purified by repeating cycles of freezing and thawing (Johnson, B. H.; Hecht, M. H. *Bio/Technology.* 1994, 12, 1357). We had applied this method to the purification of FucIso, but in our case the protein was not obtained in a completely pure form (FIG. 5, lane 1). Further purification by FPLC using a Mono Q column (anion exchange) with a gradient between 0.2 and 0.5 M of NaCl provided the enzyme in a completely pure form (FIG. 5, lane 2). The specific activity calculated from this preparation is 746.9 U/mg of protein.

Vectors.

The vector pKK223-3 was obtained from Pharmacia Biotech Inc. (Piscataway, N.J.). The vector pKK223-3 (used to clone FucIso) contains the strong Tac promoter which is also regulated by the lac repressor and induced by the addition of IPTG to the medium.

Microorganism.

*Escherichia coli* K12 (ATCC 10798) was obtained from American Type Culture Collection. The host strain *E. coil*

XL1-Blue MRF' was purchased from Stratagene Co. (San Diego, Calif.). The microorganisms were maintained on LB (Luria-Bertani) medium. When host strains harbored with plasmids, the LB medium containing 250 µg/mL of ampicillin was used. Stock cultures were kept as cell suspension at −70° C. in 30% glycerol solution.

PCR Amplification.

The DNA of *E. coli* K12 was extracted according to the method described by Maniatis et al (Maniatis, T., Fritsch, E. F., Sambrook, *J. Molecular Cloning: A laboratory manual*, 1989, Cold Spring Harbor Laboratory, Cold Spring Harbor, N.Y.). PCR amplification was performed in a 100 µL reaction mixture containing 1 µL (1.5 µg) of DNA template, 300 nmoles of the corresponding primers, 200 µM of dNTPs, 50 mM KCl, 10 mM Tris-HCl (pH 8.3), 2 mM $MgCl_2$, 0.01% gelatin, 0.1% Triton X-100, and 2 units of *Thermus aquaticus* DNA polymerase (Stratagene Co.). The reaction was overlayed with mineral oil and subjected to 30 cycles of amplifications. The cycle conditions were set as follows: denaturation at 94° C. for 1 min, annealing at 60° C. for 1.5 min and elongation at 72° C. for 1.5 min.

Construction of the Expression Vectors.

The DNA insert obtained from the PCR amplification was purified on 0.8% agarose gel. The DNA band corresponding to the target gene was cut and purified with QIAEX gel extraction kit (Qiagen Co., Chatworth, Calif.) and eluted with TE buffer (10 mM Tris-HCl and 1 mM EDTA, pH 7.5). The DNA corresponding to FucIso was digested with EcoRI and PstI (all the restriction enzymes were from Boehringer Mannheim Biochemical Co.) for 2 hours at 37° C. The digested DNA was then recovered by phenol/chloroform extraction and ethanol precipitation (70% of final ethanol concentration containing 10% of 3N Na-acetate, pH 5.2), and purified by agarose (0.8%) gel electrophoresis as above. This DNA was used as insert. The vector pKK223-3 was digested with EcoRI and PstI. Then the vector was recovered with ethanol precipitation after extraction with phenol/chloroform. The restriction enzyme-digested vector was further purified on agarose gel as described above. The insert was then ligated with the vector with T4 DNA ligase. The expression plasmids constructed in this way were then transformed into *E. coli* XL1-Blue MRF' strain and plated on LB agar plates containing 250 µg/mL ampicillin.

Screening for Positive Clones.

Between 20 and 25 colonies were randomly selected for each gene. The plasmids were isolated using the QIAprep-spin Plasmid Kit (Qiagen Inc.). The isolated plasmids were digested with the corresponding restriction enzymes and analyzed on agarose gel to confirm the presence of the gene insert. The positive clones were selected and used for protein expression.

Expression of Recombinant Proteins.

To express the desired protein, the positive clone was grown on 100 mL of LB medium containing 250 µg/mL ampicillin at 37° C. with shaking (300 rpm). After the cell growth reached a point where the turbidity was about 0.5 as measured by the absorbance at 600 nm ($OD_{600}$), this culture was transferred to a fresh LB medium (1 L) containing 250 µg/mL ampicillin and incubated until $OD_{600}$=0.4–0.5, then IPTG was added to reach a final concentration of 150 µM to induce the expression of the target protein. Different temperatures of culture after induction were applied in order to optimize the conditions for the expression of the recombinant protein. The expression level of FucIso was analyzed at different times after induction until a total of 18 h of culture. In the case of the RhamIso the cells were harvested when the $OD_{600}$, was about 2.0 (3 h when the cells were grown at 30° C. after induction, 4 h when the temperature was 25° C. and 18 h at 20° C.).

Analysis of Inclusion Bodies.

The presence of inclusion bodies was analyzed according to the procedure describe by Maniatis et al (Maniatis, T., Fritsch, E. F., Sambrook, *J. Molecular Cloning: A laboratory manual*, 1989, Cold Spring Harbor Laboratory, Cold Spring Harbor, N.Y. 12. Marston, F. A. O; Lowe, P. A.; Doel, J. M.; Schoemaker, S.; White, S.; Angal, S. *Bio/Technology*, 1984, 2, 800). Cells from 1 L culture were centrifuged (10,000×g, 30 min, 4° C.), and the pellet was suspended in Tris-HCl buffer (50 mM pH 7.5) containing 8 µL of 50 mM phenylmethylsulfonylfluoride (PMSF) and 4 mg of deoxycholic acid per g of cell. The cells were disrupted by a French press at 16,000 lb/$in^2$ and centrifuged at 16,000×g for 30 min. The pellet was resuspended in Tris-HCl buffer (50 mM, pH 8.0) containing 10 mM EDTA and 0.5% of Triton X-100. After incubation for 5 min at room temperature, the sample was centrifuged at 12,000×g for 15 min. Finally, the pellet obtained in this way was resuspended in 10 mL of distilled water. The presence of the recombinant protein in the supernatants and/or pellet was checked by SDS-PAGE in a Phastsystem (Pharmacia Co.) using precast gels with a 10–15% gradient of polyacrylamide in the separation zone.

Solubilization of Inclusion Bodies.

The inclusion bodies present in the pellet obtained as described above were solubilized by addition of urea to a final concentration of 6 M. After 1-h incubation at room temperature, the suspension was centrifuged at 12,000×g for 30 min. The urea was removed slowly by dialysis against a total of 12 L of Tris-HCl buffer (50 mM, pH 7.6) with three changes in 36 h. After dialysis the sample was again centrifuged as above.

Purification of the FucIso.

The crude extract of the FucIso was prepared, with slight modifications, according to the procedure of Johnson and Hecht (Johnson, B. H.; Hecht, M. H. *Bio/Technology*. 1994, 12, 1357). The cells obtained from 1 L cultures were frozen in a dry-ice/ethonal bath for 3 min, and then the sample was thawed by immersion in an ice/water for 10 min. These steps were repeated 3 more times. Then the cells were gently resuspended in Tris-HCl buffer (50 mM, pH 7.6) and kept in an ice/water bath for another 30 min. Finally the sample was centrifuged at 10,000×g for 4 min. Further purification of the FucIso was done on FPLC using an anion exchange Mono Q column. The sample was eluted with a gradient of NaCl between 0.2 and 0.5 M in Tris-HCl (50 mM, pH 7.6). Fractions containing proteins were detected by absorbance at 280 nm. The fractions containing FucIso were pooled and the NaCl removed using Centripep tubes (Amicon Co.) with MW cut off of 10,000. The enzyme purity was determined by SDS-PAGE using precast gels with a gradient of polyacrylamide in the separation zone of 10–15%.

Enzyme Activity Assay.

The activity of the isomerase was assayed using the ketose as substrate and measuring its disappearance by the cysteine-carbazol method (Jung, S.-H.; Jeong, J.-H.; Miller, P.; Wong, C.-H. *J. Org. Chem*. 1994, 241, 3028). The reaction mixture in the case of the FucIso contained 1.2 µmol of glycine buffer (pH 9.3), 0.05 µmol of $MnCl_2$, 5 µmol of L-fuculose and a certain amount of the enzyme in a total volume of 100 µL. The mixture was incubated at 37° C. and aliquots of 5 µL were taken at different times in a period of 10 min. The calibration curve for the ketoses was done using L-fuculose synthesized as described infra. One unit of enzyme activity is defined as the quantity that catalyzes the formation of 1 μmole of aldose per minute under the condition assayed. The protein concentration was determined using the BCA kit from Pierce. The samples were incubated during 30 min at 37° C. and the absorbance measured at 562 nm. The calibration curve was obtained using the concentrations of BSA between 25 and 2,000 μg/mL.

Scheme 1

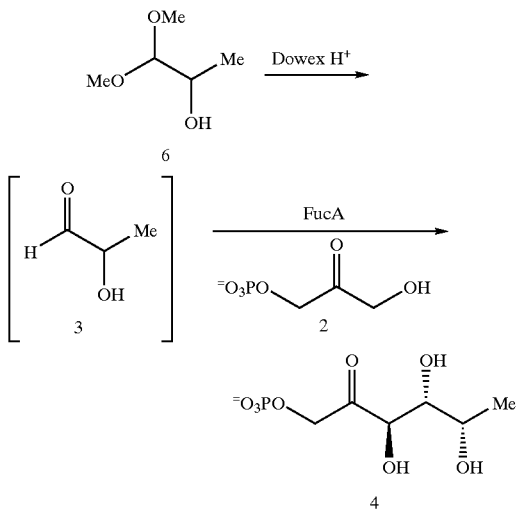

Stepwise Synthesis of 1. L-Fuculose 1-Phosphate Barium Salt 4

A chemo-enzymatic synthetic route for producing L-fucose is illustrated in Scheme 1. Compound 6, the starting material, is produced according to the procedure described by Drueckhammer et al. (Durrwachter, J. R.; Drueckhammer, D. G.; Nozaki, K.; Sweers, H. M.; Wong, C.-H. *J. Am. Chem. Soc.* 1986, 108, 7812.) Compound 6 (1.51 g; 12.6 mmol) was dissolved in purified water (13 mL) and treated at 50° C. for 8 h and the resin was filtered off and washed with water (2×5 mL). A solution of dihydroxyacetone phosphate 2 as prepared in Jung, S.-H.; Jeong, J.-H.; Miller, P.; Wong, C.-H. *J. Org. Chem.* 1994, 59, 7182, was added (5.76 mL; 2.10 mmol) and the pH was adjusted to 6.8 with 6N NaOH (0.6 mL). L-fuculose aldolase crude extract (63 units; 6.5 mL as prepared in Wong, C.-H. et. al. *Bioorg. Med. Chem.* 1995, 3, 945.) was added and the mixture was stirred at room temperature until 91% of 2 was consumed as assayed from the procedure of Bergmeyer, H. U. *Methods of Enzymatic Analysis*, 3rd Ed., Vol 2, Verlag Chemie: Deerfield, Fla., 1984, pp 146–7. After adjusting the pH to 7.0 with 2N NaOH, $BaCl_2 \cdot 2H_2O$ (1.03 g, 2 equiv.) was added and the mixture was stirred for 1 h at room temperature. The precipitate was centrifuged (30 min×4500 rpm) and the supernatant was decanted, treated with acetone (2 vol) and the mixture kept at 4° C. overnight. The precipitate was collected by centrifugation (30 min×4500 rpm), washed with $Et_2O$/ethanol (1:1) (10 mL) and dried under high vacuum. A white solid of crude L-fuculose-1-phosphate 4 (0.64 g, 80%) was obtained. This salt was used without further purification for the next step (Straub, A.; Effenberger, F.; Fischer, P. *J. Org. Chem.* 1990, 55, 3926).

Synthesis of L-Fuculose 5

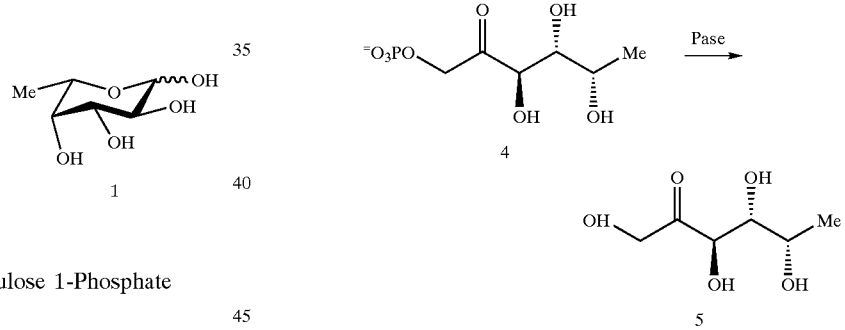

Crude L-fuculose-1-phosphate 4 (0.50 g) was powdered, dispersed in $H_2O$ (9 mL) and treated with Dowex 50W-X8 resin ($H^+$ form, 400 mesh) until pH 2.8 for 30 min. The resin was filtered off, washed with water (2×2 mL) and the filtrate was adjusted to pH 4.7 with 6N $HC_1$. Acid phosphatase (250 units) was added, the mixture was heated at 37° C. for 21 h, the pH was adjusted to 7.0 with saturated $Ba(OH)_2$ soln. and methanol (2 vol) was added. The precipitate was filtered off through Celite and the solvent removed under reduced pressure. The residue was chromatographed on silica gel with $CHCl_3$/Methanol (3:1). Compound 5 (123 mg, 46% from DHAP) was obtained as a slightly yellowish oil: $[\alpha]=0°$ (c 1, water), $[\alpha]_D=0°$ (c 1.9, water)]. NMR ($^1H$ and $^{13}C$) data were in accordance with literature values reported in Liu, K. K.-C.; Xajimoto, T.; Chen, L.; Zhong, Z.; Ichikawa, Y.; Wong, C.-H. *J. Org. Chem.* 1991, 56, 6280, A sample was taken and converted to the 2-nitrophenylhydrazone derivative: m. p. 158–160° C. (Lit. Green, M.; Cohen, S. S. *J. Biol. Chem.* 1956, 219, 557 which reports m.p. as 162–163° C.).

Synthesis of L-Fucose 1

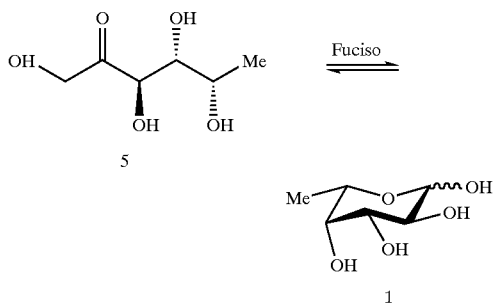

Compound 5 (89.6 mg; 0.546 mmol) obtained as described supra was dissolved in Tris-HCl buffer (50 mM, pH 7.5; 2 mL) containing mercaptoethanol (2 mM) and MnCl$_2$ (2 mM). An aliquot of the L-fucose isomerase crude extract (preparation described infra), (1 mL, 820 units) was added and the mixture was stirred overnight at room temperature. Methanol (2 vol) was added and the mixture was filtered through Celite. The solvent was distilled under reduced pressure and the residue chromatographed on Dowex 50W-X8 resin (Barium form, 400 mesh, 2.5×9.5 cm) with water/ethanol (1:1). Compound 1 (75.2 mg, 84%) was obtained as a yellowish oil: $[\alpha]_{Deg}$=−73.5° (c 1.1, water), [Lit. $[\alpha]_{Deg}$=−77° (c 1, water), Lit. [α]Deg=−80° (c 0.35, water), Lit. $[\alpha]_{Deg}$=−76.1° (c 0.65, water), Lit. $[\alpha]_{Deg}$=−75° (c 0.8, water)]. NMR ($^1$H and $^{13}$C) data were identical to those from an authentic sample. Literature values from Dejter-Juszynski, M.; Flowers, H. M. *Carbohydr. Res.* 1973, 28, 144; Chiba, T.; Tejima, S. *Chem. Pharm. Bull.* 1979, 27, 2838; Gesson, J.-P.; Jaquesy, J.-C.; Mondon, M.; Petit, P. *Tetrahedron Lett.* 1992.

Sequential Synthesis of 1. Compound 6 (1.21 g; 10.1 mmol) was dissolved in water (3 mL) and Dowex 50W-X8 (H$^+$ form, 200–400 mesh) was added until pH 2.8. The mixture was heated at 50° C. for 8 h, then the resin was filtered off and washed with water (2×0.5 mL). A solution of 2, as synthesized by Wong, C.-H. et. al. *J. Org. Chem.* 1994, 59, 7182, (4.62 mL, 1.68 mmol) was added and the mixture was adjusted to pH 6.8 with 6N NaOH (0.4 mL). L-fuculose aldolase (5.2 mL, 50 units) previously prepared by Wong, C.-H. et. al. *Bioorg. Med. Chem.* 1995, 3, 945, was added, the mixture was stirred gently at room temperature for 17 h (DHAP analysis indicates 95% conversion) and the pH was adjusted to 4.7 with 6N HCl (0.4 mL). Acid phosphatase (0.45 mL, 225 units) was added and the mixture heated at 37° C. for 19 h. The mixture was cooled to room temperature and the pH was adjusted to 7.5 with 6N NaOH (0.6 mL). MnCl$_2$ (30 μl, 0.7 M) and L-fucose isomerase (3 mL, 2460 units) were added. The mixture was stirred at room temperature for 24 h and adjusted to pH 7.0 with 2N HCl. Methanol (2 vol) was then added and the precipitate was filtered off through Celite. The solvent was removed under reduced pressure and the residue chromatographed on silica gel with CHCl$_3$/methanol (3:1). The fractions containing L-fucose 1 were pooled, then concentrated and the residue chromatographed on Dowex 50W-X8 (Barium form, 200–400 mesh) with water/ethanol (1:1) to yield 1 as a white-yellowish solid (152 mg, 0.927 mmol, 55.2%). NMR ($^1$H and $^{13}$C) data were identical to those of an authentic sample: m. p. 134–136° C., [Lit. 137–138° C., Lit. 152–153° C., Lit. 139–140° C., Lit. 137–139° C.]; $[\alpha]_{Deg}$=−74.1° (c=1.1, water), [Lit. $[\alpha]_{Deg}$32 77° (c=1, water), Lit. $[\alpha]_{Deg}$=−80° (c=0.35, water), Lit. $[\alpha]_{Deg}$=−76.1° (c 0.65, water), Lit. $[\alpha]_{Deg}$=−750° (c 0.8, water)]. Literature values from Dejter-Juszynski, M.; Flowers, H. M. *Carbohydr. Res.* 1973, 28, 144; Chiba, T.; Tejima, S. *Chem. Pharm. Bull.* 1979, 27, 2838; Gesson, J.-P.; Jaquesy, J.-C.; Mondon, M.; Petit, P. *Tetrahedron Lett.* 1992.

Scaled up sequential synthesis of 1. Compound 6 (6.0 g, 50 mmol) was hydrolyzed in water (50 mL) with Dowex 50W-X8 resin (H$^+$ form, 200–400 mesh, 6.0 g, pH 2.8) for 4 h at 60° C. After the resin was filtered off and washed with water, a solution of 2 (18.60 mL, 10.0 mmol, synthesized by Wong, C.-H. *J. Org. Chem.* 1994, 59, 7182) was added, the mixture adjusted to pH 6.8 with 6N NaOH (1.8 mL) and L-fuculose aldolase (24 mL, 305 units) was added. The mixture was readjusted to pH 6.8 with 6N NaOH (0.2 mL) and the solution was degassed with argon and protected from light. After 3 h at room temperature (DHAP analysis indicates 95% conversion) the mixture was adjusted to pH 4.7 with 6N HCl (1.8 mL), acid phosphatase (1.33 mL, 400 units) was added and the mixture heated at 37° C. for 18 h. The mixture was then cooled to room temperature and adjusted to pH 7.5 with 6N NaOH (2.6 mL). MnCl$_2$ (1 ml, 0.11 M) and L-fucose isomerase (4 mL, 3280 units) were added. The mixture was stirred at room temperature for 9 h and adjusted to pH 7.0 with 6N HCl. Methanol (2 vol) was then added and the precipitate was filtered off through Celite and washed with MeOH (4×25 mL). MeOH was removed under reduced pressure (bath temp. <25° C.) and water (100 mL) was added on the aqueous residue and the mixture was continuously extracted with AcOEt for 48 h. The organic extract was discarded and the aqueous solution evaporated under reduced pressure (bath temp. <25° C.). The residue was treated with methanol (50 mL) and the white solid formed was filtered off, washed with more methanol (2×15 mL) and discarded. Charcoal was added to the filtrate and the mixture heated at 30° C. for 15 min. After filtration to remove charcoal, methanol was removed and toluene was added time to time to remove traces of water (bath temp. <25° C.). After removing the solvents, the residue was dissolved in hot absolute ethanol (12.5 mL), seeded with 1 and stored at 4° C. for 2 days. Compound 1 (543 mg, 3.3 mmol, 33.1%) was obtained as a white solid whose physical and spectroscopic data were in accordance with those from an authentic sample: m. p. 139–140° C.; $[\alpha]_D$=−76.6° (c=0.9, water).

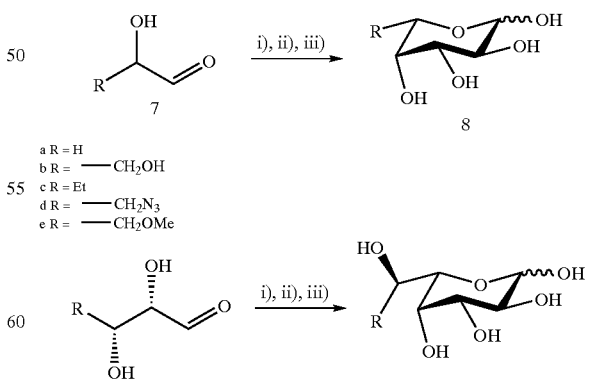

Scheme 2 a R = H
b R = —CH$_2$OH
c R = Et
d R = —CH$_2$N$_3$
e R = —CH$_2$OMe

9a R = Me
10a i) Fuculose aldolase/DHAP, ii) Acid phosphatase.
iii) Fucose isomerase.

Synthesis of D-Arabinose 8a

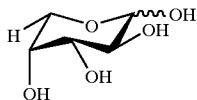

Synthesis of D-Arabinose 8a. A synthetic route for producing D-arabinose 8a is illustrated in Scheme 2. Compound 7a from Aldrich (12.6 mmol) was dissolved in purified water (13 mL) and treated at 50° C. for 8 h and the resin was filtered off and washed with water (2×5 mL). A solution of dihydroxyacetone phosphate 2 as prepared in Jung, S.-H.; Jeong, J.-H.; Miller, P.; Wong, C.-H. *J. Org. Chem.* 1994, 59, 7182, was added (5.76 mL; 2.10 mmol) and the pH was adjusted to 6.8 with 6N NaOH (0.6 mL). L-fuculose aldolase crude extract (63 units; 6.5 mL as prepared in Wong, C.-H. et. al. *Bioorg. Med. Chem.* 1995, 3, 945.) was added and the mixture was stirred at room temperature until 91% of 2 was consumed as assayed from the procedure of Bergmeyer, H. U. *Methods of Enzymatic Analysis*, 3rd Ed., Vol 2, Verlag Chemie: Deerfield, Fla., 1984, pp 146–7. After adjusting the pH to 7.0 with 2N NaOH, $BaCl_2 \cdot 2H_2O$ (1.03 g, 2 equiv.) was added and the mixture was stirred for 1 h at room temperature. The precipitate was centrifuged (30 min×4500 rpm) and the supernatant was decanted, treated with acetone (2 vol) and the mixture kept at 4° C. overnight. The precipitate was collected by centrifugation (30 min×4500 rpm), washed with $Et_2O$/ethanol (1:1) (10 mL) and dried under high vacuum. A white solid of crude was obtained. This salt was used without further purification for the next step (Straub, A.; Effenberger, F.; Fischer, P. *J. Org. Chem.* 1990, 55, 3926).

The crude material from the previous step, was powdered, dispersed in $H_2O$ (9 mL) and treated with Dowex 50W-X8 resin ($H^+$ form, 400 mesh) until pH 2.8 for 30 min. The resin was filtered off, washed with water (2×2 mL) and the filtrate was adjusted to pH 4.7 with 6N HCl. Acid phosphatase (250 units) was added, the mixture was heated at 37° C. for 21 h, the pH was adjusted to 7.0 with saturated $Ba(OH)_2$ soln. and methanol (2 vol) was added. The precipitate was filtered off through Celite and the solvent removed under reduced pressure. The residue was chromatographed on silica gel with $CHCl_3$/Methanol (3:1).

The compound obtained was then dissolved in Tris-HCl buffer (50 mM, pH 7.5; 2 mL) containing mercaptoethanol (2 mM) and $MnCl_2$ (2 mM). An aliquot of the L-fucose isomerase crude extract (preparation described infra), (1 mL, 820 units) was added and the mixture was stirred overnight at room temperature. Methanol (2 vol) was added and the mixture was filtered through Celite. The solvent was distilled under reduced pressure and the residue chromatographed on Dowex 50W-X8 resin (Barium form, 400 mesh, 2.5×9.5 cm) with water/ethanol (1:1). Compound 8a (80 mg, 0.54 mmol, 30%). NMR ($_1$H and $_{13}$C) data were identical to those of an authentic sample. $[\alpha]_D=-19°$ (c=0.5, MeOH, 30 min) $[[\alpha]_D=-104.3°$ (c=3, water, 20 h) from Aldrich Co.].

Synthesis of L-Galactose 8b

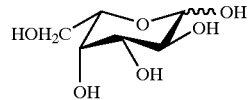

L-Galactose 8b. A synthetic route for producing L-galactose 8b is illustrated in Scheme 2. Compound 7b (1.21 g; 10.1 mmol prepared and described in Henderson, I., Sharpless, K. B, Wong C. H., *J. Am. Chem. Soc.* 1994, 116, 558) was dissolved in water (3 mL) and Dowex 50W-X8 ($H^+$ form, 200–400 mesh) was added until pH 2.8. The mixture was heated at 50° C. for 8 h, then the resin was filtered off and washed with water (2×0.5 mL). A solution of 2, as synthesized by Wong, C.-H. et. al. *J. Org. Chem.* 1994, 59, 7182, (4.62 mL, 1.68 mmol) was added and the mixture was adjusted to pH 6.8 with 6N NaOH (0.4 mL). L-fuculose aldolase (5.2 mL, 50 units) previously prepared by Wong, C.-H. et. al. *Bioorg. Med. Chem.* 1995, 3, 945, was added, the mixture was stirred gently at room temperature for 17 h (DHAP analysis indicates 95% conversion) and the pH was adjusted to 4.7 with 6N HCl (0.4 mL). Acid phosphatase (0.45 mL, 225 units) was added and the mixture heated at 37° C. for 19 h. The mixture was cooled to room temperature and the pH was adjusted to 7.5 with 6N NaOH (0.6 mL). $MnCl_2$ (30 μl, 0.7 M) and L-fucose isomerase (3 mL, 2460 units) were added. The mixture was stirred at room temperature for 24 h and adjusted to pH 7.0 with 2N HCl. Methanol (2 vol) was then added and the precipitate was filtered off through Celite. The solvent was removed under reduced pressure and the residue chromatographed on silica gel with $CHCl_3$/methanol (3:1). The fractions containing 8b were pooled, then concentrated and the residue chromatographed on Dowex 50W-X8 (Barium form, 200–400 mesh) with water/ethanol (1:1) to yield 8b as a white-yellowish solid (60 mg, 0.32 mmol, 58%). NMR ($_1$H and $_{13}$C) data were identical to those of an authentic sample. $[\alpha]_D=-70.2°$ (c=1, water), $[[\alpha]_D=-77°$ (c=1, water) from Aldrich Co.].

Synthesis of 6-Methyl-L-fucose 8c

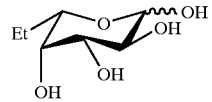

6-Methyl-L-fucose 8c. A synthetic route for producing 6-methyl-L-fucose 8c is illustrated in Scheme 2. Compound 7c, the starting material, was produced according to procedure described by Whitesides et. al. (*J.Org.Chem.* 1992, 57, 5899.) Compound 7c (1.51 g; 12.6 mmol) was dissolved in purified water (13 mL) and treated at 50° C. for 8 h and the resin was filtered off and washed with water (2×5 mL). A solution of dihydroxyacetone phosphate 2 as prepared in Jung, S.-H.; Jeong, J.-H.; Miller, P.; Wong, C.-H. *J. Org. Chem.* 1994, 59, 7182, was added (5.76 mL; 2.10 mmol) and the pH was adjusted to 6.8 with 6N NaOH (0.6 mL). L-fuculose aldolase crude extract (63 units; 6.5 mL as prepared in Wong, C.-H. et. al. *Bioorg. Med. Chem.* 1995, 3, 945.) was added and the mixture was stirred at room temperature until 91% of 2 was consumed as assayed from the procedure of Bergmeyer, H. U. *Methods of Enzymatic Analysis*, 3rd Ed., Vol 2, Verlag Chemie: Deerfield, Fla., 1984, pp 146–7. After adjusting the pH to 7.0 with 2N NaOH, $BaCl_2 \cdot 2H_2O$ (1.03 g, 2 equiv.) was added and the mixture was stirred for 1 h at room temperature. The precipitate was centrifuged (30 min×4500 rpm) and the supernatant was decanted, treated with acetone (2 vol) and the mixture kept at 4° C. overnight. The precipitate was collected by centrifugation (30 min×4500 rpm), washed with Et$_2$O/ethanol (1:1) (10 mL) and dried under high vacuum. A white solid of crude (0.64 g, 80%) was obtained. This salt was used without further purification for the next step (Straub, A.; Effenberger, F.; Fischer, P. *J. Org. Chem.* 1990, 55, 3926).

The crude from the previous step (0.50 g) was powdered, dispersed in H$_2$O (9 mL) and treated with Dowex 50W-X8 resin (H$^+$ form, 400 mesh) until pH 2.8 for 30 min. The resin was filtered off, washed with water (2×2 mL) and the filtrate was adjusted to pH 4.7 with 6N HCl. Acid phosphatase (250 units) was added, the mixture was heated at 37° C. for 21 h, the pH was adjusted to 7.0 with saturated Ba(OH)$_2$ soln. and methanol (2 vol) was added. The precipitate was filtered off through Celite and the solvent removed under reduced pressure. The residue was chromatographed on silica gel with CHCl$_3$/Methanol (3:1). The product (123 mg, 46% from DHAP) was obtained as a slightly yellowish oil.

The product from the previous step (89.6 mg; 0.546 mmol) was dissolved in Tris.HCl buffer (50 mM, pH 7.5; 2 mL) containing mercaptoethanol (2 mM) and MnCl$_2$ (2 mM). An aliquot of the L-fucose isomerase crude extract (preparation described infra), (1 mL, 820 units) was added and the mixture was stirred overnight at room temperature. Methanol (2 vol) was added and the mixture was filtered through Celite. The solvent was distilled under reduced pressure and the residue chromatographed on Dowex 50W-X8 resin (Barium form, 400 mesh, 2.5×9.5 cm) with water/ethanol (1:1). Compound 8c (75.2 mg, 84%) was obtained as a yellowish oil: (89 mg, 0.50 mmol, 25%). [α]$_D$=−47.6 (c=0.5, MeOH, 30 min), [Lit. [α]$_{Deg}$=−26.2° (c=1, pyridine), Lit [α]Deg=−33° (c=1.2, water)]. $^1$H-NMR (400 MHZ, D$_2$O) δ (ppm): 5.03 (H1α, d, J$_{H1α,H2α}$=3.7 Hz), 4.39 (H1β, d, J$_{H1β,H2β}$=8 Hz), 3.73 (H5α, m), 3.69 (H4α, H4β, d, J=3 Hz), 3.66 (H3α, d, J$_{H2α,H3α}$=3.5 Hz), 3.62 (H2α, d, J$_{H2α,H3α}$=3.5 Hz), 3.45 (H3β, dd, J$_{H2β,H3β}$=10 Hz, J$_{H3β,H4β}$=3–5 Hz), 3.35 (H5β, t, J$_{H5β,CH2}$=3 Hz), 3.29 (H2β, dd, J$_{H1β,H2β}$=8 Hz, J$_{H2β,H3β}$=10 Hz), 1.4–1.51 (CH$_2$, α and β), 0.77 (CH$_3$, α and β). $^{13}$C-NMR (100 MHZ, D$_2$O) δ (ppm): 96.42 (C1β), 92.23 (C1α), 76.43, 73.15, 72.04, 69.72 (β anomer), 71.81, 70.22, 69.51, 68.45 (α anomer), 23.01 (CH$_2$, α and β), 9.41 (CH$_3$, α and β). HRMS Calcd for C$_7$H$_{14}$O$_5$+H$^+$ 179.0919, found 179.0914.

Synthesis of 6-Azido-L-fucose 8d

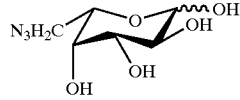

6-Azido-L-fucose 8d. A route for synthesizing 6-azido-L-fucose is illustrated in Scheme 2. Compound 7d, the starting material, was obtained according to the procedure of Wong et. al (*J. Org. Chem.*, 1988, 53, 4175.) Compound 7d (1.21 g; 10.1 mmol) was dissolved in water (3 mL) and Dowex 50W-X8 (H$^+$ form, 200–400 mesh) was added until pH 2.8. The mixture was heated at 50° C. for 8 h, then the resin was filtered off and washed with water (2×0.5 mL). A solution of 2, as synthesized by Wong, C.-H. et. al. *J. Org. Chem.* 1994, 59, 7182, (4.62 mL, 1.68 mmol) was added and the mixture was adjusted to pH 6.8 with 6N NaOH (0.4 mL). L-fuculose aldolase (5.2 mL, 50 units) previously prepared by Wong, C.-H. et. al. *Bioorg. Med. Chem.* 1995, 3, 945, was added, the mixture was stirred gently at room temperature for 17 h (DHAP analysis indicates 95% conversion) and the pH was adjusted to 4.7 with 6N HCl (0.4 mL). Acid phosphatase (0.45 mL, 225 units) was added and the mixture heated at 37° C. for 19 h. The mixture was cooled to room temperature and the pH was adjusted to 7.5 with 6N NaOH (0.6 mL). MnCl$_2$ (30 μl, 0.7 M) and L-fucose isomerase (3 mL, 2460 units) were added. The mixture was stirred at room temperature for 24 h and adjusted to pH 7.0 with 2N HCl. Methanol (2 vol) was then added and the precipitate was filtered off through Celite. The solvent was removed under reduced pressure and the residue chromatographed on silica gel with CHCl$_3$/methanol (3:1). The fractions containing 8d were pooled, then concentrated and the residue chromatographed on Dowex 50W-X8 (Barium form, 200–400 mesh) with water/ethanol (1:1) to yield 9d as a white-yellowish solid (31 mg, 0.15 mmol, 20%). [α]$_D$=−3.25 (c=0.4, MeOH, 10 min), [Lit.$^{37}$, [α]$_{Deg}$=−56.4 (c=1, H$_2$O)]. $^1$H-NMR (400 MHZ, D$_2$O) δ: 5.10 (H1α, d, J$_{H1α,H2α}$=3.7 Hz), 4.42 (H1β, d, J$_{H1β,H2β}$=8 Hz), 4.10 (H5α, ddd, J$_{H4α,H5α}$=1 Hz, J$_{CH2,H5α}$=4.6 Hz, J$_{CH2,H5α}$=8.7 Hz), 3.78 (H4α, dd, J$_{H4α,H5α}$=1 Hz, J$_{H4α,H3α}$=3 Hz), 3.72 (H4β, dd, J$_{H4β,H5β}$=1 Hz, J$_{H4β,H3β}$=3.5 Hz), 3.68 (H3α, dd, J$_{H4α,H3α}$=3 Hz, J$_{CH2α,H5β}$=10.5 Hz), 3.64 (H5β, ddd, J$_{H5β,H4β}$=1 Hz, J$_{CH2,H5β}$=4.4 Hz, J$_{CH2,H5β}$=8.4 Hz), 3.62 (H2α, dd, J$_{H2α,H1α}$=3.7 Hz, J$_{H2α,H3α}$=10.5 Hz), 3.48 (H3β, dd, J$_{2β,H3β}$=10 Hz, J$_{H3β,H4β}$=3.5 Hz), 3.31 (H2β, dd, J$_{H1β,H2β}$=8 Hz, J$_{H2β,H3β}$=10 Hz). $^{13}$C-NMR (100 MHz, D$_2$O) δ (ppm); 96.45 (C1β), 92.36 (C1α), 73.43, 72.67, 71.71, 69.11 (β anomer), 69.65, 69.03, 68.90, 68.21 (α anomer), 50.91 (C6α), 50.74 (C6β). HRMS Calcd for C$_6$H$_{11}$N$_2$O$_5$+H$^+$=206.06986, observed: 206.0693.

6-Methoxy-L-fucose 8e

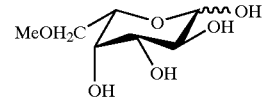

A method for synthesizing 6-methyl-L-fucose is illustrated in Scheme 2. Compound 7e, the starting material, was synthesized according to the method of Wong et. al. (*J. Am. Chem. Soc.*, 1986, 108, 7812, (1.21 g; 10.1 mmol). Compound 7e was dissolved in water (3 mL) and Dowex 50W-X8 (H$^+$ form, 200–400 mesh) was added until pH 2.8. The mixture was heated at 50° C. for 8 h, then the resin was filtered off and washed with water (2×0.5 mL). A solution of 2, as synthesized by Wong, C.-H. et. al. *J. Org. Chem.* 1994, 59, 7182, (4.62 mL, 1.68 mmol) was added and the mixture was adjusted to pH 6.8 with 6N NaOH (0.4 mL). L-fuculose aldolase (5.2 mL, 50 units) previously prepared by Wong, C.-H. et. al. *Bioorg. Med. Chem.* 1995, 3, 945, was added, the mixture was stirred gently at room temperature for 17 h (DHAP analysis indicates 95% conversion) and the pH was adjusted to 4.7 with 6N HCl (0.4 mL). Acid phosphatase (0.45 mL, 225 units) was added and the mixture heated at 37° C. for 19 h. The mixture was cooled to room temperature and the pH was adjusted to 7.5 with 6N NaOH (0.6 mL). MnCl$_2$ (30 μl, 0.7 M) and L-fucose isomerase (3 mL, 2460 units) were added. The mixture was stirred at room temperature for 24 h and adjusted to pH 7.0 with 2N HCl. Methanol (2 vol) was then added and the precipitate was filtered off through Celite. The solvent was removed under reduced pressure and the residue chromatographed on silica gel with CHCl₃/methanol (3:1). The fractions containing L-fucose 8e were pooled, then concentrated and the residue chromatographed on Dowex 50W-X8 (Barium form, 200–400 mesh) with water/ethanol (1:1) to yield 8e as a white-yellowish solid (63 mg, 0.3 mmol, 25%). $[\alpha]_D=-14.4$ (c=1, MeOH, 4 h), [Lit, $[\alpha]_{25eq}=-80.6$ (c=1, pyridine, eq)]. ¹H-NMR (400 MHz, D₂O) δ: 5.10 (H1α, d, $J_{H1\alpha,H2\alpha}=3.6$ Hz), 4.42 (H4β, d, $J_{H1\beta,H2\beta}==8$ Hz), 4.08 (H5α, t, $J_{CH2,H5\alpha}=6$ Hz), 3.81 (H4α, d, $J_{H4\alpha,H3\alpha}=3$ Hz), 3.75 (H4β, d, $J_{H4\beta,H3\beta}=3.5$ Hz), 3.6–3.7 (H2α, H3α, H5β, overlapped signals), 3.58 (CH₃O—, α and β), 3.47–3.52 (H3β and CH₂ α and β, overlapped signals), 3.32 (H2β, dd, $J_{H1\beta,H2\beta}=8$ Hz, $J_{H2\beta,H3\beta}=10$ Hz) ¹³C-NMR (100 MHz, D₂O) δ (ppm): 96.31 (C1β), 92.19 (C1α), 73.17, 72.61, 71.82, 71.61, 69.46, 68.93, 68.44, 68.19, 59.29 (CH₃), 58.35 (C6β), 58.20 (C6α). HRMS Calcd for $C_7H_{14}O_6+Na^+$ 217.0688, observed 217.0647.

phosphatase (0.45 mL, 225 units) was added and the mixture heated at 37° C. for 19 h. The mixture was cooled to room temperature and the pH was adjusted to 7.5 with 6N NaOH (0.6 mL). MnCl₂ (30 μl, 0.7 M) and L-fucose isomerase (3 mL, 2460 units) were added. The mixture was stirred at room temperature for 24 h and adjusted to pH 7.0 with 2N HCl. Methanol (2 vol) was then added and the precipitate was filtered off through Celite. The solvent was removed under reduced pressure and the residue chromatographed on silica gel with CHCl₃/methanol (3:1). The fractions containing L-fucose 1 were pooled, then concentrated and the residue chromatographed on Dowex 50W-X8 (Barium form, 200–400 mesh) with water/ethanol (1:1) to yield 1 as a white-yellowish solid (18 mg, 0.09 mmol, 28%). ¹H-NMR (major β pyranose form, D₂O) δ; 4.55.(dd, 1H, J=7.6 and 4.5 Hz); 4.02 (m, 1H); 3.82 (t, 1H, J=3.2 Hz),;3.62 (dd, 1H, J=10.0 and 3.0 Hz); 3.49 (t, 1H, J=7.9 Hz); 3.37 (d, J=7.3

Scheme 3

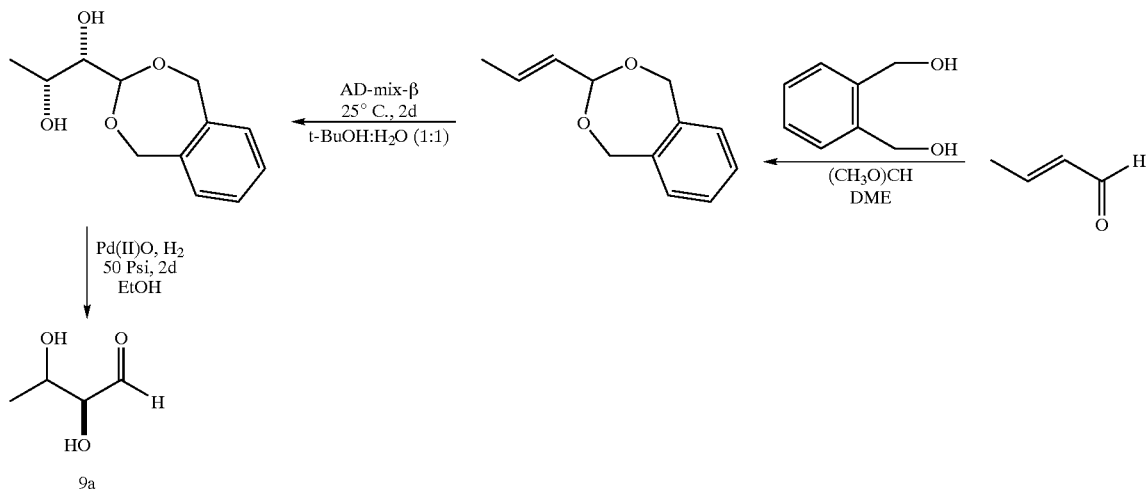

Hz, 1H); 1.22 (d, H., J=6.4 Hz) ppm. ¹³ C-NMR (major β piranose form, D₂O) δ 95.5, 78.3, 72.1, 70.9, 67.9, 66.0, 16.7 ppm. HRMS calcd for $C_7H_{14}O_6+Na^+$ 217.0688, found 217.0691.

Synthesis of 7-Deoxy-D-glycero-L-galactoheptose 10a

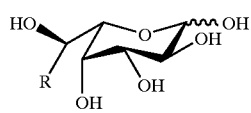

10a

7-Deoxy-D-glycero-L-galactoheptose 10a A method for synthesizing 7-deoxy-D-glycero-L-galactoheptose 10a is illustrated in Scheme 2. Compound 9a, the starting material, was synthesized was synthesized according to the methodology illustrated in Scheme 3 and outlined infra. Compound 9a (1.21 g; 10.1 mmol) was dissolved in water (3 mL) and Dowex 50W-X8 (H⁺ form, 200–400 mesh) was added until pH 2.8. The mixture was heated at 50° C. for 8 hours, then the resin was filtered off and washed with water (2×0.5 mL). A solution of 2, as synthesized by Wong, C.-H. et. al. *J. Org. Chem.* 1994, 59, 7182, (4.62 mL, 1.68 mmol) was added and the mixture was adjusted to pH 6.8 with 6N NaOH (0.4 mL). L-fuculose aldolase (5.2 mL, 50 units) previously prepared by Wong, C.-H. et. al. *Bioorg. Med. Chem.* 1995, 3, 945, was added, the mixture was stirred gently at room temperature for 17 h (DHAP analysis indicates 95% conversion) and the pH was adjusted to 4.7 with 6N HCl (0.4 mL). Acid Synthesis of 3-(1-Propenyl)-1,5-dihydro-3H-2,4-benzodioxepine

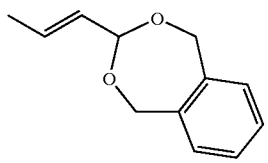

A method for synthesizing 3-(1-propenyl)-1,5-dihydro-3H-2,4-benzodioxepine is illustrated in Scheme 3. 1,2-Benzenedimethanol (500 mg, 3.62 mmol) and p-toluenesulfonic acid (172 mg, 0.9 mmol) were dissolved in 2 mL of dry DME and triethylortoformate (0.396 mL, 3.62 mmol) was added. The solution was stirred at rt. and under argon for 1 h. Ether (20 mL) was added and the organic layer washed with a saturated solution of NaHCO₃ and water, then dried (Na₂SO₄). The solvent was evaporated giving crude 3-methoxy-1,5-dihydro-3H-2,4 benzodioxepine as a colorless oil (526 mg, 89%).

Crude 3-methoxy-1,5-dihydro-3H-2,4 benzodioxepine (361 mg, 2.2 mmol) was dissolved in dry DME (2 mL) p-toluenesulfonic acid (95.2 mg, 0.5 mmol) and chrotonaldehyde (0.166 mL, 2 mmol) were added. The mixture was stirred at rt. for 2 h. Ether (10 mL) was added and the organic layer washed with a saturated solution of $NaHCO_3$ and water, then dried ($Na_2SO_2$). After removed the solvent the crude was purified by cc using AcOEt/Hexane (1:1) as eluent. 3-(1-Propenyl)-1,5-dihydro-3H-2,4-benzodioxepine 3 was obtained as an oil (175 mg, 46%). $^1$HNMR (CDCl$_3$): δ 7.39–7.12 (m, 4H), 5.98 (dqd, J=15.5, 6.5 and 1.0 Hz, 1H), 5.53 (ddq, J=15.5, 4.7 and 1.4 Hz, 1H), 5.32 (dd, J=4.6 and 0.8 Hz, 1H), 4.94 (d, J=14.2 Hz, 2H), 4.86 (d, J=14.2 Hz, 2H), 1.74 (dqd, J=6.4, 1.5 and 0.8 Hz, h.). $^{13}$CNMR(CDCl$_3$): δ 5 138.8, 130.1, 127.8, 127.1, 127.0, 104.7, 70.0, 17.6.

Synthesis of 3(1S, 2R-dihydroxypropyl)1,5dihydro-3H-2,4 Benzodioxepine

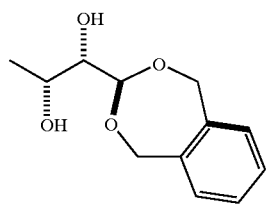

A method for synthesizing 3(1S, 2R-dihydroxypropyl) 1,5 dihydro-3H-2,4 benzodioxepine is illustrated in Scheme 3. AD-mix-β (2.148 g) and methane sulfonamide (145.8 mg, 153 mmol) were dissolved in a 1:1 mixture of t-BuOH: $H_2O$ (16 mL). Over this mixture the acetal 12 (292 mg, 1.53 mmol) was added and mixture was stirred for 2 d. Dichloromethane was added (20 mL) and the organic layer separated. The aqueous phase was extracted two more times with $CH_2Cl_2$. The combined organic fractions were dried ($Na_2SO_4$) and the solvent evaporated. Purification by cc (AcOEt/Hexane, 1:1), gave the 3(1S, 2R-dihydroxypropyl) 1,5dihydro-3H-2,4 benzodioxepine 13 as an oil (306 mg, 89%). [α]$_{D25}$ +22.75° (c 3.2, CHCl$_3$). $^1$HNMR(CDCl$_3$): δ 7.26–7.19 (m, 4H), 5.00 (d, J=5.0 Hz, 1H), 4.97 (d, J=14.0 Hz, 2H), 4.90 (dd, J=14.0 and 5.5 Hz, 2H), 4.07 (tdd, J=6.4, 5.3 and 2.0 Hz, 1H), 3.43 (ddd, J=5.7, 5.0 and 2.0 Hz, 1H), 2.61 (d, J=5.7 Hz, 1H), 2.43 (d, J=5.7 Hz, 1H), 1.26 (d, J=6.5 Hz, h.). $^{13}$CNMR(CDCl$_3$): δ 128.0, 127.94, 127.91, 127.88, 109.2, 74.5, 73.8, 73.4, 66.1, 19.6.

Synthesis of 2S, 3R-Dibydroxybutanal 9a

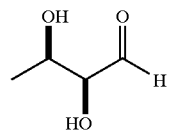

2s, 3R-dihydroxybutanal. A solution of 3(1S, 2R-dihydroxypropyl) 1,5-dihydro-3H-2,4 benzodioxepine 13 (160 mg, 0.67 mmol) in methanol, containing Pd(II)O catalyst (9.4 mg, 0.67 mmol) was hydrogenated in a Parr apparatus at 50 Psi for 2 days. The catalyst was removed by filtration and volatile removed in vacuum to give 2S, 3R-dihydroxybutanal 9a, as illustrated in Scheme 3.

What is claimed is:

1. A method for synthesizing L-fucose in a single reaction mixture comprising the following steps:

Step A: Providing L-fuculose-1-phosphate by an aldol addition reaction between dihydroxyacetone phosphate with DL-lactaldehyde, said aldol addition reaction being catalyzed by L-fuculose-1-phosphate aldolase;

Step B: Converting the L-fuculose-1-phosphate of said Step A to L-fuculose, said conversion being catalyzed by acid phosphatase (E.C. 3.1.3.2);

Step C: Converting the L-fuculose of said Step B to L-fuculose, said conversion being catalyzed by L-fucose isomerase, said L-fucose isomerase being purified recombinant L-fucose isomerase.

* * * * *

SEQUENCE LISTING

```
<160> NUMBER OF SEQ ID NOS: 4

<210> SEQ ID NO 1
<211> LENGTH: 26
<212> TYPE: DNA
<213> ORGANISM: Artificial Sequence
<220> FEATURE:
<223> OTHER INFORMATION: synthesized

<400> SEQUENCE: 1
atattctgca gaccactcaa ctggaa                                    26

<210> SEQ ID NO 2
<211> LENGTH: 32
<212> TYPE: DNA
<213> ORGANISM: Artificial Sequence
<220> FEATURE:
<223> OTHER INFORMATION: synthesized

<400> SEQUENCE: 2
ggcgcaagct tttacctgct ggcgtatcgt gt                             32

<210> SEQ ID NO 3
<211> LENGTH: 35
<212> TYPE: DNA
<213> ORGANISM: Artificial Sequence
<220> FEATURE:
<223> OTHER INFORMATION: synthesized

<400> SEQUENCE: 3
```

```
atattgaatt caacatgaaa aaaatcagct taccg                              35
```

<210> SEQ ID NO 4
<211> LENGTH: 30
<212> TYPE: DNA
<213> ORGANISM: Artificial Sequence
<220> FEATURE:
<223> OTHER INFORMATION: synthesized

<400> SEQUENCE: 4

```
gcgcctgcag ttaaacgctt gtacaacgga                                    30
```